(12) United States Patent
Thakore et al.

(10) Patent No.: US 11,857,761 B2
(45) Date of Patent: Jan. 2, 2024

(54) CHECK VALVE

(71) Applicant: CareFusion 303, Inc., San Diego, CA (US)

(72) Inventors: Bhanupratapsingh Dharmendrasingh Thakore, Vadodara (IN); Kanjimpuredathil Muralikrishna Menon, Bangalore (IN)

(73) Assignee: CareFusion 303, Inc., San Diego, CA (US)

( * ) Notice: Subject to any disclaimer, the term of this patent is extended or adjusted under 35 U.S.C. 154(b) by 263 days.

(21) Appl. No.: 17/393,269

(22) Filed: Aug. 3, 2021

(65) Prior Publication Data
US 2023/0045614 A1   Feb. 9, 2023

(51) Int. Cl.
| | |
|---|---|
| *F16K 15/02* | (2006.01) |
| *A61M 39/24* | (2006.01) |
| *A61M 5/168* | (2006.01) |
| *B08B 1/00* | (2006.01) |
| *B08B 1/02* | (2006.01) |

(52) U.S. Cl.
CPC ........ *A61M 5/16881* (2013.01); *A61M 39/24* (2013.01); *B08B 1/005* (2013.01); *B08B 1/02* (2013.01); *F16K 15/02* (2013.01); *F16K 15/023* (2013.01); *A61M 2039/246* (2013.01); *A61M 2209/10* (2013.01)

(58) Field of Classification Search
CPC .......... A61M 5/16881; A61M 2209/10; A61M 39/24; A61M 2039/246; F16K 15/02; F16K 15/023; B08B 1/005; B08B 1/02
See application file for complete search history.

(56) References Cited

U.S. PATENT DOCUMENTS

| | | | |
|---|---|---|---|
| 447,387 A | 3/1891 | Wade | |
| 2,330,881 A * | 10/1943 | Gora ..................... | F16K 15/063 |
| | | | 251/334 |

(Continued)

FOREIGN PATENT DOCUMENTS

| | | | | |
|---|---|---|---|---|
| EP | 83814 A | * | 7/1983 | ............. F16K 17/04 |
| GB | 590860 A | | 7/1947 | |

(Continued)

OTHER PUBLICATIONS

International Search Report and Written Opinion in Application No. PCT/US2022/039204 dated Oct. 28, 2022, 12 pages.

*Primary Examiner* — Marina A Tietjen
(74) *Attorney, Agent, or Firm* — Morgan, Lewis & Bockius LLP (57) ABSTRACT

Check valves are described herein. A check valve includes an inlet body, an outlet body, a valve body, a valve member, and a wiping extension. The inlet body defines an inlet portion. The outlet body defines an outlet portion. The valve body is coupled between the inlet bod and the outlet body. The valve body defines a valve cavity. The valve cavity is in fluid communication with the inlet portion and the outlet portion. The valve member is disposed within the valve cavity. The valve member is configured to permit flow from the inlet portion to the outlet portion and prevent flow from the outlet portion to the inlet portion. The wiping extension extends from the valve body toward the valve member. The wiping extension is movable relative to the valve member to dislodge particulate from the valve member.

18 Claims, 7 Drawing Sheets

(56) References Cited

U.S. PATENT DOCUMENTS

| | | | | |
|---|---|---|---|---|
| 3,409,037 A | * | 11/1968 | Nelson | F16K 17/10 |
| | | | | 92/143 |
| 3,429,338 A | * | 2/1969 | Armen | F16K 15/20 |
| | | | | 604/920 |
| 3,620,653 A | * | 11/1971 | Gaylord | F16K 15/04 |
| | | | | 137/533.15 |
| 4,548,235 A | * | 10/1985 | Rosaen | F16K 15/063 |
| | | | | 137/542 |
| 5,860,449 A | | 1/1999 | Schulte | |
| 2002/0104567 A1 | | 8/2002 | Matthews et al. | |
| 2005/0126638 A1 | | 6/2005 | Gilbert | |

FOREIGN PATENT DOCUMENTS

| | | | | |
|---|---|---|---|---|
| GB | 1085398 A | * | 9/1967 | F16K 17/04 |
| WO | WO2010107597 A1 | | 9/2010 | |

* cited by examiner

CHECK VALVE

FIELD OF THE INVENTION

The present disclosure generally relates to check valves, and, in particular, to check valves for intravenous sets.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. During operation, the flow of medical fluid can be controlled with a check valve to prevent backflow and/or mixing of medical fluids.

In some applications, particulate or other contaminants from the medical fluid can accumulate within the check valve.

SUMMARY

The disclosed subject matter relates to check valves. In certain embodiments, a check valve is disclosed that comprises an inlet body defining an inlet portion; an outlet body defining an outlet portion; a valve body coupled between the inlet body and the outlet body, the valve body defining a valve cavity therein, wherein the valve cavity is in fluid communication with the inlet portion and the outlet portion; a valve member disposed within the valve cavity, wherein the valve member is configured to permit flow from the inlet portion to the outlet portion and prevent flow from the outlet portion to the inlet portion; and a wiping extension extending from the valve body toward the valve member, wherein the wiping extension is movable relative to the valve member to dislodge particulate from the valve member.

In certain embodiments, a method is disclosed that comprises directing flow to an inlet portion of a check valve; permitting flow from the inlet portion of the check valve to an outlet portion of the check valve by moving a valve member in response to the flow to the inlet portion; and dislodging particulate disposed on the valve member by moving a wiping extension relative to the valve member In certain embodiments, a check valve is disclosed that comprises an inlet tubing; an outlet tubing; and a check valve, including: an inlet body defining an inlet portion in fluid communication with the inlet tubing; an outlet body defining an outlet portion in fluid communication with the outlet tubing; a valve body coupled between the inlet body and the outlet body, the valve body defining a valve cavity therein, wherein the valve cavity is in fluid communication with the inlet portion and the outlet portion; a valve member disposed within the valve cavity, wherein the valve member is configured to permit flow from the inlet tubing to the outlet tubing and prevent flow from the outlet tubing to the inlet tubing; and a wiping extension extending from the valve body toward the valve member, wherein the wiping extension is movable relative to the valve member to dislodge particulate from the valve member.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed check valve incorporates a wiping extension. The wiping extension can unclog or dislodge particulate from the valve member to allow particulate to be removed from the check valve. By removing particulate from the check valve, the wiping extension can ensure fluid flow, reliable operation of the check valve and reduce contamination of medical fluid that passes through the check valve, avoiding the need to replace an IV set.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed check valve, it is to be understood that this description is only an example of usage and does not limit the scope of the claims. Various aspects of the disclosed check valve may be used in any application where it is desirable to control flow of medical fluid and eliminate particulate within fluid devices.

The disclosed check valve overcomes several challenges discovered with respect to certain conventional check valves. One challenge with certain conventional check valves is that particulates or other contaminants can accumulate within the check valve. In certain applications, the accumulation of particulates can prevent the reliable operation of the check valve. Because the accumulation of particulates may result in back flow through the check valve and prevent proper dosage through an IV set, the use of certain conventional check valves is undesirable.

Therefore, in accordance with the present disclosure, it is advantageous to provide check valves as described herein that allow for particulates or other contaminants to be dislodged and/or removed from the check valve, increasing reliability, preventing back flow, and providing proper dosage to the patient. Further, the use of the check valves described herein can reduce the need to replace IV sets, minimizing clinical steps and reducing waste.

Examples of check valves that can dislodge or remove particulates from within the check valve are now described.

Figure 1:
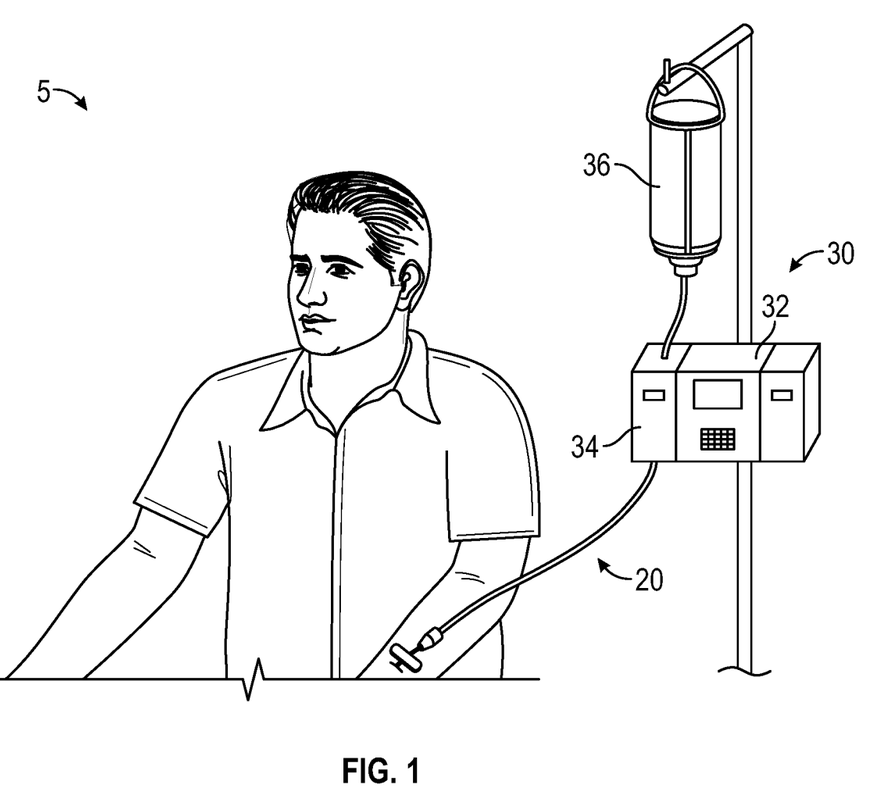
FIG. 1 depicts a patient receiving an infusion of a medical fluid using an IV pump.

FIG. 1 illustrates a patient 5 receiving an infusion of a medical fluid through an optional IV pump 30 according to certain aspects of the present disclosure. In applications that utilize an IV pump, the IV pump 30 comprises a controller 32 and two pump modules 34. An IV set 20 is connected between a container 36 of the medical fluid and the patient 5. During operation, a check valve can control the flow of medical fluid to a patient 5 to prevent the back flow of medical fluid. For example, a check valve can allow the delivery of a first medical fluid (e.g., saline) and a second medical fluid (e.g., a drug) to a patient while preventing the back flow of either medical fluid during the administration of the first medical fluid and the second medical fluid. In some embodiments, the check valve can be disposed in between or in line with tubing of the IV set 20.

Figure 2:
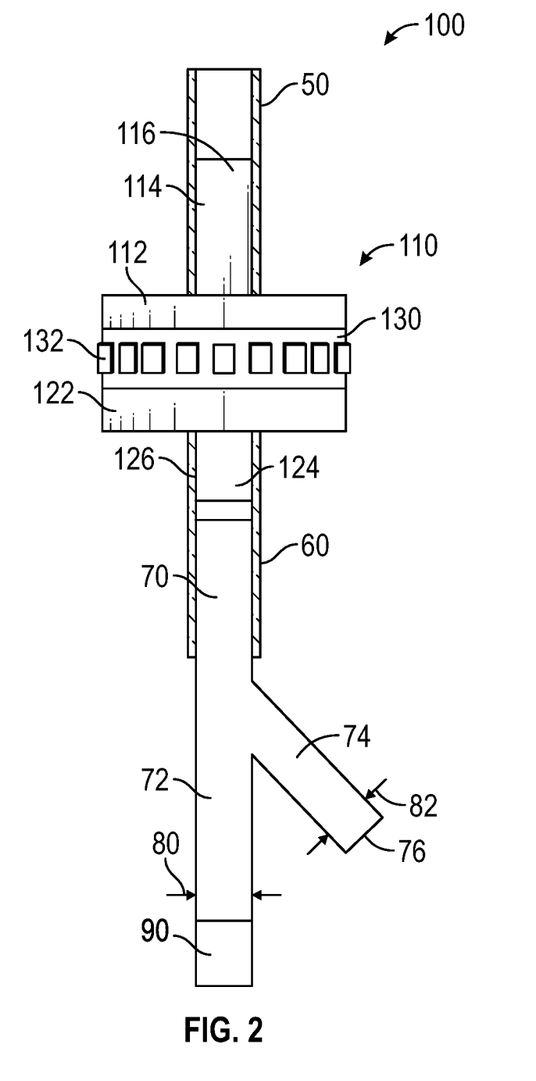
FIG. 2 illustrates a check valve assembly according to certain aspects of the present disclosure.

FIG. 2 illustrates a check valve assembly 100 according to certain aspects of the present disclosure. In the depicted example, the check valve assembly 100 controls the flow of medical fluid through the inlet tubing 50 and the outlet tubing 60. During operation, a check valve 110 can allow fluid flow from the inlet tubing 50 to the outlet tubing 60. Further, the check valve 110 can prevent or reduce back flow from the outlet tubing 60 to the inlet tubing 50. In some embodiments, the outlet tubing 60 can direct flow toward the patient 76 via the patient flow path 74 of the outlet flow path 70.

As described herein, the check valve 110 can allow for particulates or other contaminants to be dislodged and/or removed from within the check valve 110. In some embodiments, dislodged or removed particulates can be directed to a reservoir 90 in fluid communication with the check valve 110. The reservoir 90 can be in fluid communication with the check valve 110 via the reservoir flow path 72 of the outlet flow path 70.

During the dislodging or removal of the particulates within the check valve 110, the patient flow path 74 can be obstructed by a clamp 82 to prevent particulates from flowing toward the patient 76. During normal operation of the check valve 110 (e.g., when particulate is not being removed), the reservoir flow path 72 can be obstructed by a clamp 80 to prevent the flow of medical fluid into the reservoir 90 and direct medical fluid toward the patient 76.

Figure 3:
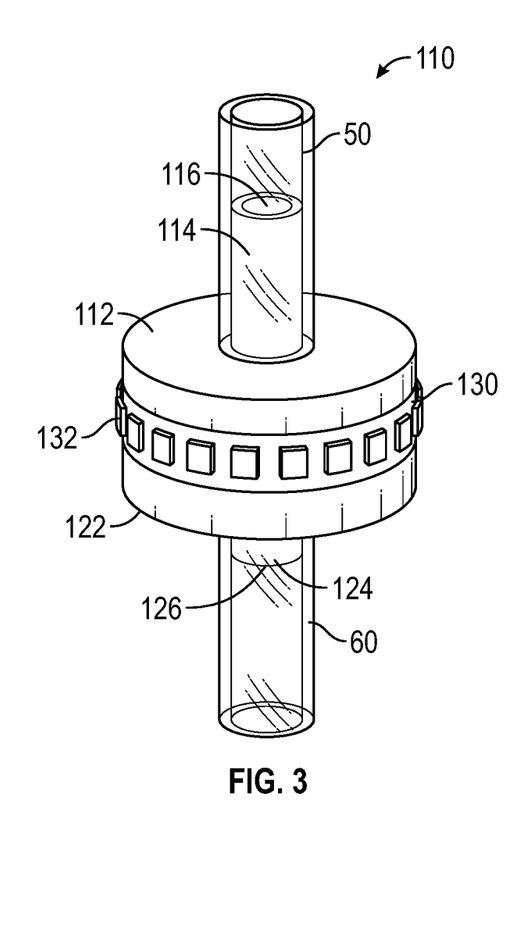
FIG. 3 illustrates a perspective view of the check valve of FIG. 2.
Figure 4:
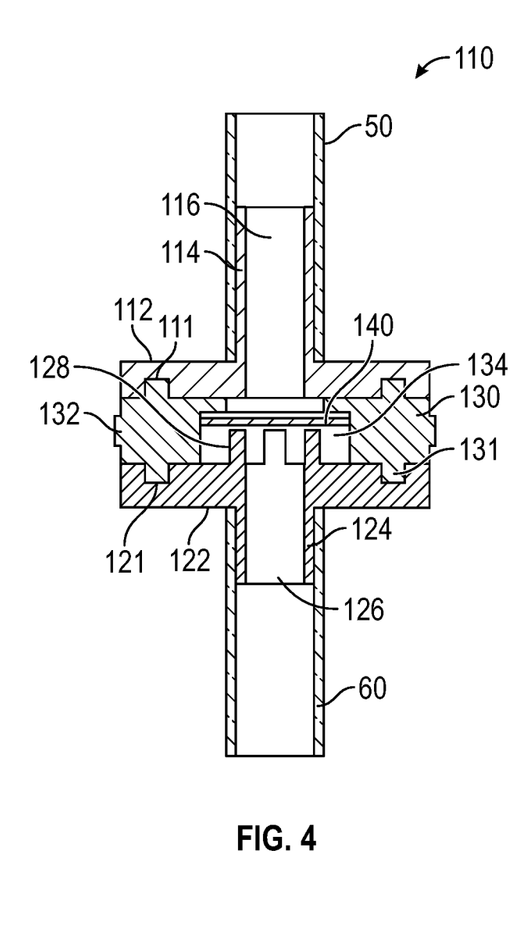
FIG. 4 illustrates a cross-sectional view of the check valve of FIG. 2.

FIG. 3 illustrates a perspective view of the check valve 110 of FIG. 2. FIG. 4 illustrates a cross-sectional view of the check valve 110 of FIG. 2. With reference to FIGS. 2-4, as described herein, the check valve 110 controls the flow of medical fluid between an inlet 114 and an outlet 124.

As illustrated, the check valve 110 receives fluid flow from inlet tubing 50 coupled to the inlet portion 112. In the depicted example, the inlet portion 112 defines an inlet 114 that is in fluid communication with the inlet tubing 50 to receive fluid flow from a fluid source, such as a medical fluid container. In the depicted example, the inlet 114 defines an inlet lumen 116 to permit fluid communication with the inlet tubing 50.

In some embodiments, the inlet portion 112 can be formed from a polymer (rigid or soft), including, but not limited to, methylmethacrylate acrylonitrile butadiene styrene (MABS), styrene acrylonitrile (SAN), or polycarbonate.

Flow received by the inlet 114 can be directed toward a valve body 130 to control the flow through the check valve 110. As illustrated, the inlet portion 112 can be disposed adjacent to, or above the valve body 130.

During operation, fluid flow from the inlet portion 112 is received by the valve body 130. The valve body 130 defines a valve cavity 134 to receive fluid flow from the inlet portion 112 and control the direction of the fluid flow through the check valve 110. In the depicted example, the valve cavity 134 is in fluid communication with the inlet 114 of the inlet portion 112.

In some embodiments, the valve body 130 can be formed from a polymer, including, but not limited to, MABS, SAN, or polycarbonate.

During operation, fluid from the valve cavity 134 is directed to the outlet tubing 60 coupled to the outlet portion 122. The outlet portion 122 defines an outlet 124 that is in fluid communication with the outlet tubing 60 to allow fluid to pass downstream to a patient or another portion of the IV set. In the depicted example, the outlet 124 defines an outlet lumen 126 to permit fluid communication with the outlet tubing 60. As can be appreciated, the outlet lumen 126 is in fluid communication with the valve cavity 134 to allow fluid to pass from the inlet portion 112, through the valve body 130, and through the outlet portion 122.

In some embodiments, the outlet portion 122 can be formed from a polymer, including, but not limited to, MABS, SAN, or polycarbonate. As illustrated, the outlet portion 122 can be disposed adjacent to, or below the valve body 130.

In the depicted example, the check valve 110 includes a valve member 140 to control the direction of flow through the valve cavity 134. As illustrated, the valve member 140 is disposed within the valve cavity 134 to allow flow from the inlet portion 112 toward the outlet portion 122 and prevent or reduce flow from the outlet portion 122 toward the inlet portion 112.

In the depicted example, the valve member 140 is movable relative to the valve cavity 134 to allow flow from the inlet portion 112 toward the outlet portion 122 and/or to prevent or reduce flow from the outlet portion 122 toward the inlet portion 112. For example, portions (e.g., edges) of the valve member 140 can move away from the walls of the valve cavity 134 to allow flow from the inlet portion 112 toward the outlet portion 122. In the presence of back flow, portions of the valve member can move toward and/or engage and seal with the walls of the valve cavity to prevent or reduce flow from the outlet portion 122 toward the inlet portion 112.

Optionally, the valve member 140 can be deformable to move relative to the valve cavity 134. For example, the valve member 140 can be configured to deform in response to the direction of flow. Therefore, the valve member 140 may deform to permit flow from the inlet portion 112 toward the outlet portion 122 and may deform to prevent or reduce flow from the outlet portion 122 toward the inlet portion 112. In some embodiments, the valve member 140 can be formed from a deformable material such as silicone, or any other suitable material, including, phthalate- and latex-free materials.

The valve member 140 may have any size and shape that may permit the valve member 140 to flex or bend under fluid pressure and permit forward flow of the fluid (from the inlet portion 112 to the outlet portion 122) through the check valve 110, and occlude reverse flow of the fluid (from the outlet portion 122 to the inlet portion 112) through the check valve 110. The valve member 140 may be a disk, plate, a diaphragm or similar, and may be square, rectangular, circular, elliptical, oblong, and the like. The shape and size of the valve member 140 is not limited to any particular shape or size.

In some embodiments, the valve member 140 can be supported on a pedestal formed by one or more posts 128. The posts 128 can be spaced apart to define a portion of the passageway within the valve cavity 134. In some embodiments, the posts 128 can extend from the outlet portion 122 and into the valve cavity 134.

Figure 5:
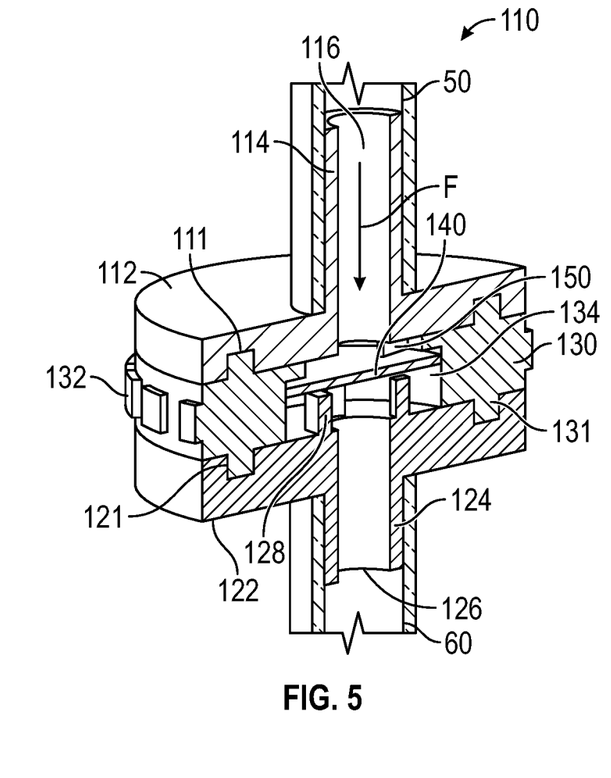
FIGS. 5 and 6 illustrate a cross-sectional view of the check valve of FIG. 2 during fluid flow operation.
Figure 6:
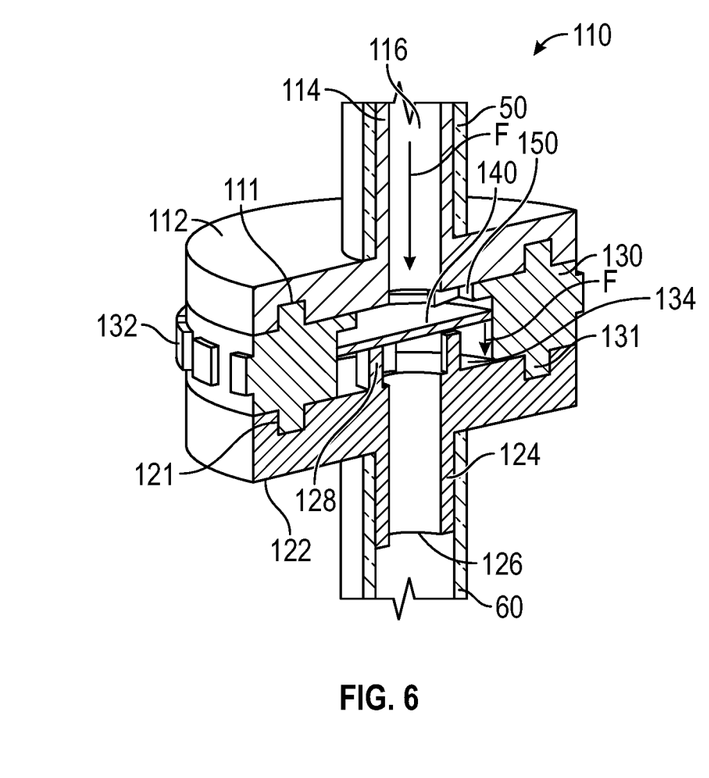

FIGS. 5 and 6 illustrate a cross-sectional view of the check valve 110 of FIG. 2 during fluid flow operation. With reference to FIGS. 2-6, during operation, fluid flow F may enter the check valve 110 via inlet tubing 50 coupled to the inlet 114. The fluid flow F may flow through the inlet lumen 116 and into the valve cavity 134. The valve member 140 permits the fluid flow F to pass through the valve cavity 134. The fluid flow F can exit the check valve 110 through the outlet 124. The outlet lumen 126 can direct the fluid flow F from valve cavity 134 to the outlet tubing 60. As can be appreciated, the fluid flow F can be directed toward the patient.

Figure 7:
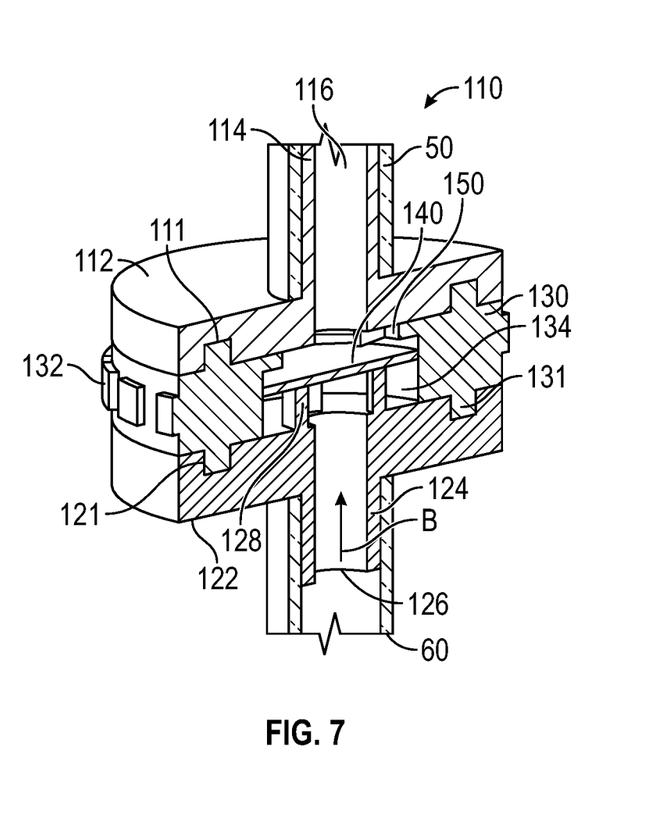
FIGS. 7 and 8 illustrate a cross-sectional view of the check valve of FIG. 2 during back flow operation.
Figure 8:
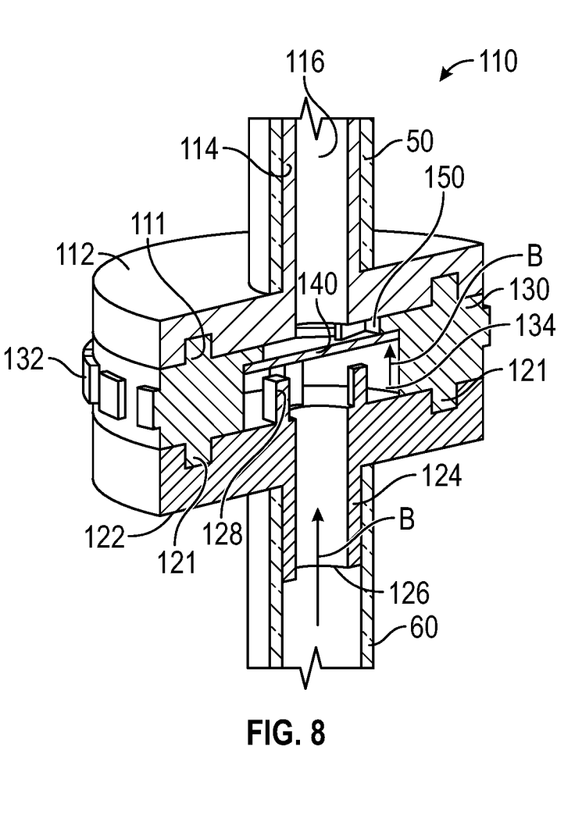

FIGS. 7 and 8 illustrate a cross-sectional view of the check valve 110 of FIG. 2 during back flow operation. With reference to FIGS. 2-4, 7, and 8, during operation, backflow B from the outlet tubing 60 is prevented from entering the inlet tubing 50. In the event that backflow B enters the check valve 110 via the outlet tubing 60 coupled to the outlet 124, the backflow B can flow into the lower portion of the valve cavity 134. However, the valve member 140 prevents the backflow B from entering the upper portion of the valve cavity 134, and in turn, the inlet portion 112 of the check valve 110. As described herein, the valve member 140 can seal against the walls of the valve cavity 134 to prevent the backflow B from passing through the valve cavity 134.

Figure 9:
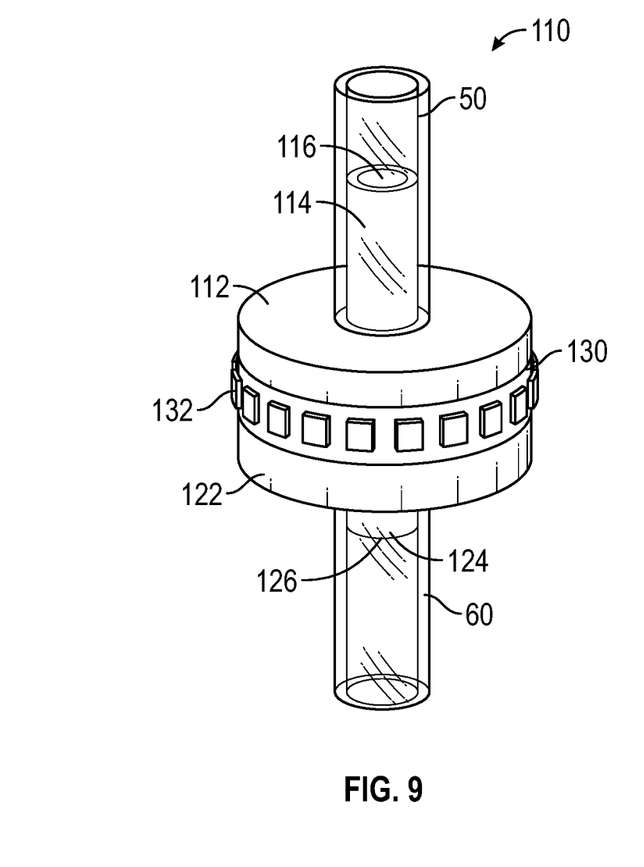
FIG. 9 illustrates a perspective view of the check valve of FIG. 2.
Figure 10:
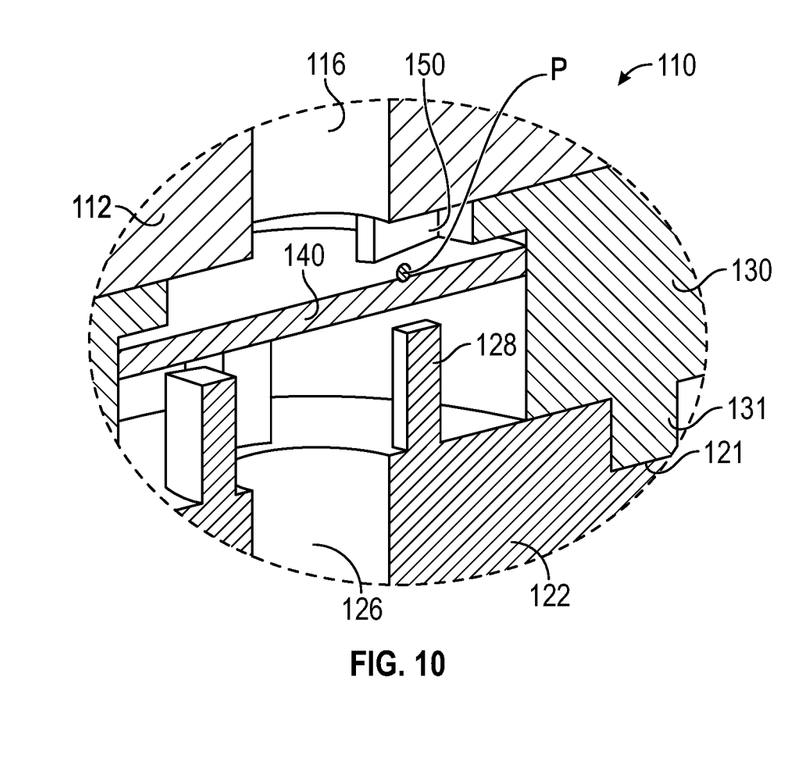
FIG. 10 illustrates a cross-sectional detail view of the check valve of FIG. 2.

FIG. 9 illustrates a perspective view of the check valve 110 of FIG. 2. FIG. 10 illustrates a cross-sectional detail view of the check valve 110 of FIG. 2. As described herein, during operation, contaminants, sediment, grit, or other particulate P can accumulate on the valve member 140 of the check valve 110, causing undesirable operation of the check valve 110. Advantageously, the check valve 110 allows for the particulate P to be cleared, dislodged, or otherwise removed from the valve member 140 and/or the check valve 110 generally to allow for proper operation of the check valve 110 and locking of the fluid line.

In the depicted example, particulate P accumulated on the valve member 140 can be dislodged by a wiping extension 150 configured to extend toward the valve member 140 and dislodge particulate P disposed on a surface of the valve member 140. In some embodiments, the wiping extension 150 can extend to contact the surface of the valve member 140 and skim or scrape the valve member 140 without damaging the surface of the valve member 140. In some embodiments, the wiping extension 150 can be spaced apart from the surface of the valve member 140 to prevent contact with the valve member 140 but permit particulate P to be dislodged from the valve member 140. As illustrated, the wiping extension 150 can extend from an upper portion of the valve cavity 134 and toward an upper surface of the valve member 140. Optionally, the wiping extension 150 can extend downward from the valve body 130 of the check valve 110 and into the valve cavity 134.

During a clearing or dislodging operation, the wiping extension 150 can be moved relative to the valve member 140 to scrape, skim, wipe, or dislodge any accumulated particulate P from the valve member 140. For example, the wiping extension 150 can be rotated relative to the valve member 140 to allow the wiping extension 150 to dislodge any particulate P from the valve member 140.

In the depicted example, the valve body 130 can be rotated to move or rotate the wiping extension 150 relative to the valve member 140. In some embodiments, the valve body 130 can be rotated relative to the inlet portion 112 and/or the outlet portion 122 to allow the wiping extension 150 to rotate relative to the valve member 140. Optionally, the inlet portion 112 and/or the outlet portion 122 can remain stationary relative the rotating valve body 130.

As illustrated in FIGS. 4-8 and 10, the valve body 130 can include valve body lips 131 to engage with the inlet portion 112 and/or the outlet portion 122. The valve body lips 131 can allow the valve body 130 to be coupled to the inlet portion 112 and/or the outlet portion 122 while allowing the valve body 130 to rotate relative to the inlet portion 112 and/or the outlet portion 122. For example, an upper valve body lip 131 can engage with an inlet portion groove 111 of the inlet portion 112 to allow the valve body 130 to rotate relative to the inlet portion 112. Further, the engagement of the upper valve body lip 131 with the inlet portion groove 111 can guide the rotation of the valve body 130 relative to the inlet portion 112. Similarly, a lower valve body lip 131 can engage with an outlet portion groove 121 of the outlet portion 122 to allow the valve body 130 to rotate relative to the outlet portion 122. The engagement of the lower valve body lip 131 with the outlet portion groove 121 can guide the rotation of the valve body 130 relative to the outlet portion 122.

In some embodiments, a clinician can rotate the valve body 130 of the check valve 110 to move the wiping extension 150 to dislodge or remove any particulate P from within the check valve 110. The outer surface of the valve body 130 can include one or more protrusions 132 to allow the clinician to securely grasp and rotate the valve body 130 relative to the check valve 110. Optionally, a motor or actuator can rotate the valve body 130 to move the wiping extension 150 dislodge or remove any particulate P within the check valve 110. As can be appreciated, a clinician, motor, or actuator can move the valve body 130 and therefore the wiping extension 150 at a regular interval or in response to the accumulation of particulates P.

As described herein, dislodged or removed particulates P can flow through the outlet 124 of the check valve 110 and into the outlet tubing 60. In some applications, the dislodged particulates P can be collected in a reservoir 90 (as described with respect to FIG. 2).

Figure 11:
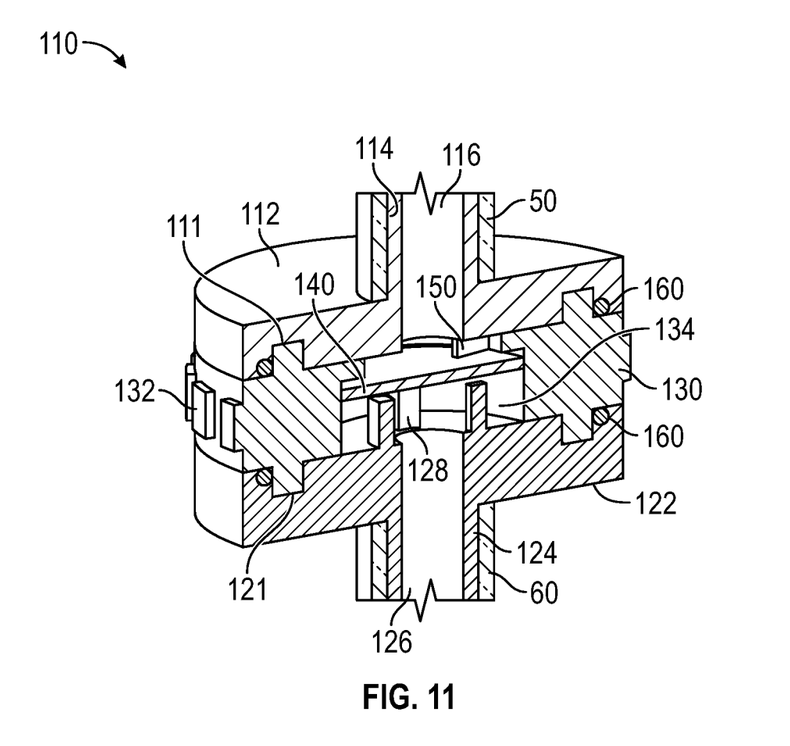
FIG. 11 illustrates a cross-sectional view of the check valve of FIG. 2.

FIG. 11 illustrates a cross-sectional view of the check valve 110 of FIG. 2. In some embodiments, the check valve 110 includes one or more seals 160 to prevent fluid leaks between the components of the check valve 110. For example, the seals 160 can prevent fluid leaks between the interface of the inlet portion 112 and the valve body 130 and between the interface of the valve body 130 and the outlet portion 122. In some embodiments, the seals 160 allow for the valve body 130 to rotate relative to the inlet portion 112 and/or the outlet portion 122 while maintain sealing engagement or otherwise a fluid-tight seal between the interfaces between the inlet portion 112, the valve body 130, and the outlet portion 122. The seals 160 can be referred to as O-rings.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve, comprising:
   an inlet body defining an inlet portion;
   an outlet body defining an outlet portion;
   a valve body coupled between the inlet body and the outlet body, the valve body defining a valve cavity therein, wherein the valve cavity is in fluid communication with the inlet portion and the outlet portion;
   a valve member disposed within the valve cavity, wherein the valve member is configured to permit flow from the inlet portion to the outlet portion and prevent flow from the outlet portion to the inlet portion; and
   a wiping extension coupled to the valve body and extending from the valve body toward the valve member, wherein the valve body and the wiping extension are movable together relative to the valve member to allow the wiping extension to dislodge particulate from the valve member.

2. The check valve of claim 1, wherein the wiping extension engages against an upper surface of the valve member.

3. The check valve of claim 1, wherein the wiping extension is spaced apart from an upper surface of the valve member.

4. The check valve of claim 1, wherein the valve body and the wiping extension are rotatable relative to the valve member.

5. The check valve of claim 1, wherein the valve body and the wiping extension are movable relative to the inlet body.

6. The check valve of claim 5, further comprising a sealing element disposed between the inlet body and the valve body.

7. The check valve of claim 1, wherein the valve body and the wiping extension are movable relative to the outlet body.

8. The check valve of claim 7, further comprising a sealing element disposed between the outlet body and the valve body.

9. The check valve of claim 1, wherein the valve body comprises an outer surface defining a plurality of protrusions, wherein the protrusions are configured to permit a user to move the valve body relative to the valve member.

10. The check valve of claim 1, wherein the valve member is movable within the valve cavity to permit flow from the inlet portion to the outlet portion and prevent flow from the outlet portion to the inlet portion.

11. The check valve of claim 10, wherein the valve member is deformable.

12. The check valve of claim 1, wherein the inlet body further defines an inlet groove.

13. The check valve of claim 12, wherein the valve body defines a valve body lip configured to engage with the inlet groove.

14. A method, comprising:
directing flow to an inlet portion of a check valve;
permitting flow from the inlet portion of the check valve to an outlet portion of the check valve by moving a valve member in response to the flow to the inlet portion; and
dislodging particulate disposed on the valve member by moving a valve body disposed between the inlet portion and the outlet portion to move a wiping extension relative to the valve member.

15. The method of claim 14, further comprising:
directing flow to the outlet portion of the check valve; and
preventing flow from the outlet portion of the check valve to the inlet portion of the check valve via the valve member in response to the flow to the outlet portion.

16. The method of claim 14, further comprising:
rotating the valve body relative to the inlet portion and the outlet portion to rotate the wiping extension relative to the valve member.

17. A check valve assembly, comprising:
an inlet tubing;
an outlet tubing; and
a check valve, comprising:
an inlet body defining an inlet portion in fluid communication with the inlet tubing;
an outlet body defining an outlet portion in fluid communication with the outlet tubing;
a valve body coupled between the inlet body and the outlet body, the valve body defining a valve cavity therein, wherein the valve cavity is in fluid communication with the inlet portion and the outlet portion;
a valve member disposed within the valve cavity, wherein the valve member is configured to permit flow from the inlet tubing to the outlet tubing and prevent flow from the outlet tubing to the inlet tubing; and
a wiping extension coupled to the valve body and extending from the valve body toward the valve member, wherein the valve body and the wiping extension are movable together relative to the valve member to allow the wiping extension to dislodge particulate from the valve member.

18. The check valve assembly of claim 17, further comprising:
an outlet flow path in fluid communication with the outlet tubing, wherein the outlet flow path defines a patient flow path configured to deliver fluid from the check valve to a patient and a reservoir flow path configured to deliver fluid and particulate from the check valve to a reservoir, wherein the patient flow path is blocked during movement of the wiping extension.

* * * * *